United States Patent [19]

Wulff

[11] 3,994,295
[45] Nov. 30, 1976

[54] HYPODERMIC SYRINGE NEEDLE MOUNTING

[76] Inventor: Goldwyn L. Wulff, 680 Nebraska SW., Huron, S. Dak. 57350

[22] Filed: Aug. 22, 1975

[21] Appl. No.: 606,769

[52] U.S. Cl. .......................... 128/215; 128/218 N; 128/221
[51] Int. Cl.² .......................................... A61M 5/00
[58] Field of Search ............... 128/215, 216, 218 R, 128/218 N, 220, 221, 239

[56] References Cited
UNITED STATES PATENTS

| | | | |
|---|---|---|---|
| 2,034,294 | 3/1936 | Hein | 128/215 |
| 2,697,437 | 12/1954 | Everett | 128/221 |
| 2,855,927 | 10/1958 | Henderson | 128/218 N |
| 3,096,763 | 7/1963 | McConnaugney et al. | 128/221 |

*Primary Examiner*—John D. Yasko
*Attorney, Agent, or Firm*—Strauch, Nolan, Neale, Nies & Kurz

[57] ABSTRACT

An adapter device for mounting a hypodermic needle on a syringe barrel consists of two telescoped elements the outer of which is a casing or shell and the inner of which is a resilient tube bonded at opposite ends to a stem adapted for connection to the barrel and a needle mounting member seated over the end of the shell.

9 Claims, 6 Drawing Figures

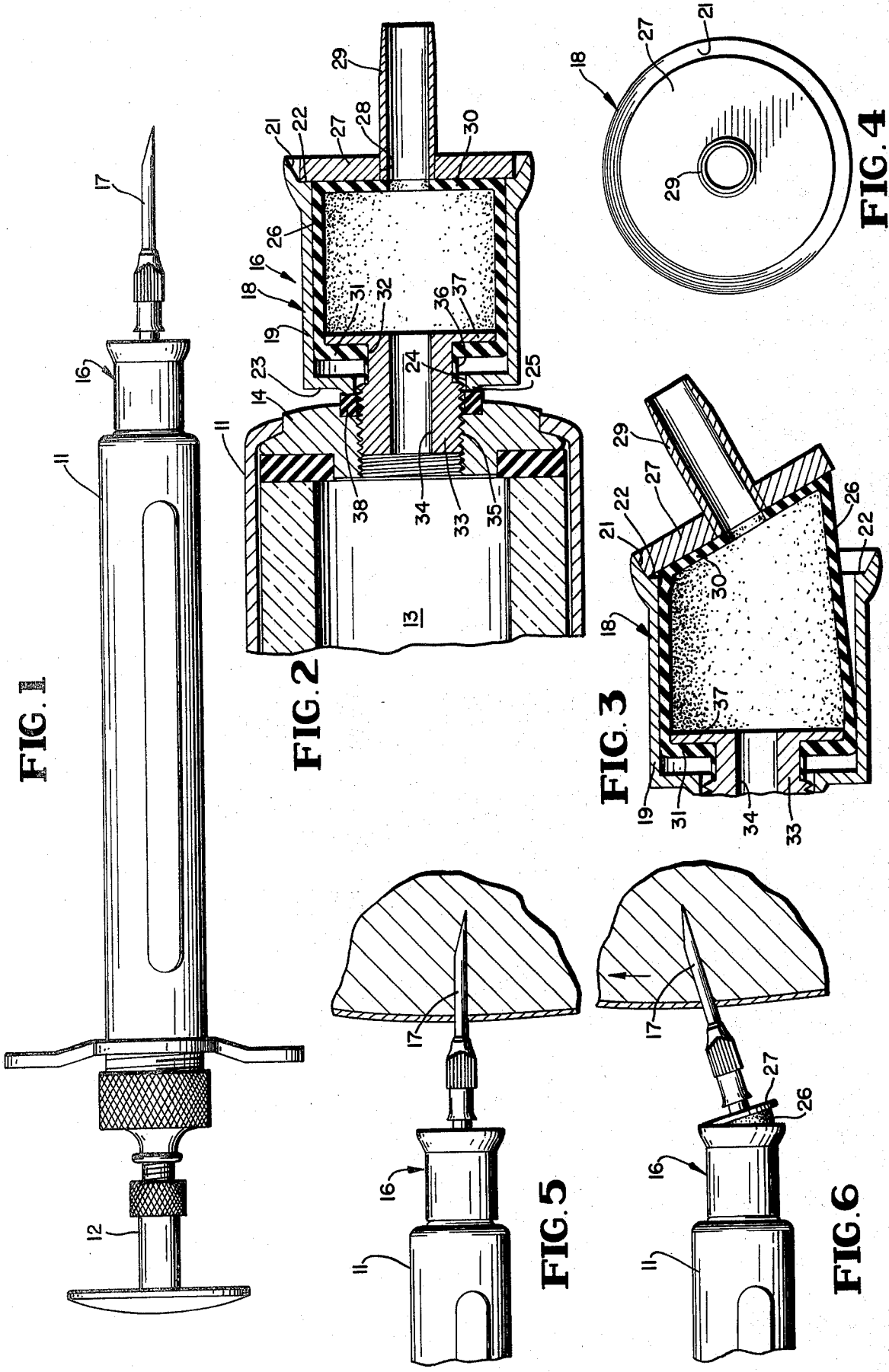

HYPODERMIC SYRINGE NEEDLE MOUNTING

This invention relates to hypodermic syringes and particularly to a novel needle mounting arrangement that enables the needle to be thrust into an animal with required force but is sufficiently flexible to prevent the needle from breaking off or bending when the animal moves during treatment.

The problems attendant to hypodermic injection of treatment or like material into large free-to-move animals have been recognized, and they are discussed and two of the proposed solutions are disclosed in U.S. Pat. Nos. 3,780,734 and 3,884,230 which show that the art has developed at least to the extent of providing flexible needle mounting in general and special guards for aid in retaining needle alignment.

The present invention represents an improvement over the foregoing in that substantially any conventional hypodermic needle may be mounted on substantially any conventional syringe by means of an adapter device of special non-complex structure and mode of operation that provides for relatively solid initial penetration into the animal's hide while permitting controlled flexure to compensate for uncontrolled animal movement, and this is a major object of the invention.

A further object of the invention lies in the provision of a novel needle mounting in an adapter device wherein the needle is mounted on a tiltable resiliently controlled support at the front end of a relatively rigid syringe barrel end attachment.

Another object of the invention is to provide a novel adapter device for mounting a hypodermic needle on a syringe barrel wherein a relatively stiff casing connected at its rear end to said barrel is lined with a tube of resilient material that has one open end fixed within the casing and the other open end secured to a relatively rigid needle mounting member seated over the open front end of the casing.

Another object of the invention is the provision of a novel adapter device for flexibly mounting a hypodermic needle on a syringe barrel wherein a needle mounting member is normally resiliently maintained on a seat coaxial with the barrel by a flexible tube that also serves to convey fluid from the barrell to the needle.

Further novel features and other objects of this invention will become apparent from the following detailed description, discussion and the appended claims taken in conjunction with the accompanying drawings.

BRIEF DESCRIPTION OF DRAWINGS

FIG. 1 is a side elevation of a hypodermic assembly incorporating an embodiment of the invention;

FIG. 2 is an enlarged fragmentary view in cross section showing detail of the flexible needle support;

FIG. 3 is a fragmentary view in section like FIG. 2 but showing the needle mounting member tilted;

FIG. 4 is an end view of the needle mounting adapter device;

FIG. 5 is a fragmentary view showing the parts during initial penetration; and

FIG. 6 shows the parts of FIG. 5 in the position where the needle is tilted by animal movement.

PREFERRED EMBODIMENTS

FIG. 1 shows a conventional type hypodermic syringe having a barrel 11 containing a reciprocable plunger (not shown) operated by a handle 12 projecting from one end, and FIG. 2 shows at 13 the discharge end of the chamber containing the liquid to be discharged. At the discharge end barrel 11 has a cap 14 provided with an internally threaded bore 15, and it is in this bore that the usual needle mounting adapter is threadedly attached.

In the invention the adapter device of the invention indicated at 16 is mounted at the same location, and a conventional type needle 17 is mounted on adapter 16.

Adapter device 16 consists essentially of two elements. One is an external casing 18 in the form of a stiff usually metal shell having a cylindrical wall 19 that terminates at one end in an outwardly flared inclined annular lip 21. An axially facing flat shoulder 22 is provided in the barrel at the small end of lip 21. At its other end the barrel is formed with a generally radial integral end wall 23 having a central small diameter opening 24 surrounded by a narrow annular ledge 25.

The other or internal element of the adapter device is a unitary composite structure comprising a self-supporting tubular preferably cylindrical body 26 of relatively stiff synthetic rubber or some resilient plastic material having bonded thereto at its front or discharge end a rigid preferably metal flat disc 27 provided with a central small diameter opening 28 from which rigidly projects a short needle attachment tube 29. As shown in FIG. 2 body 26 has an apertured inturned front wall 30 that is permanently bonded as by vulcanizing flush to the inner side of disc 27, which disc is in effect a flange on the inner end of tube 29.

At its other end body 26 has a generally radial integral end wall 31 and a central opening 32 through which extends rigid metal stem 33 having a central small diameter bore 34, an externally threaded section 35, a reduced diameter section 36 where it projects through bore 34, and a disc-like flange 37 that is disposed internally in contact with the inner side of wall 31 and permanently bonded thereto as by vulcanizing.

Thus the internal element of adapter device 16 consists of a resilient walled hollow body having bonded to it at one end a threaded hollow stem for attaching the device to the barrel of the syringe and at the other end a relatively rigid needle mounting member. This internal element is fluid tight except for discharge opening 28 at one end and the stem bore 34 at the other end.

The dimensions of the internal element are such that in assembly it may be axially thrust into the flared end of casing 18 so that end wall 31 is disposed near the casing end wall 23 with stem 33 projecting through opening 24, and with disc 27 disposed within the surrounding confines of lip 21 and effectively seated on shoulder 22.

The resilient body 26 is self-sustaining against normal collapse and in the assembly it essentially is disposed as a friction fitting liner within the cylindrical casing wall 19, and the casing wall thereby provides a co-extensive backing for body 26 when the latter contains liquid under pressure in operation as will appear. The stem threads at 35 are of conventional size to fit with threads 15 of the barrel 11 and, after the adapter elements are assembled in telescoping relation, a resilient washer 38 is placed around stem 35 and adapter device 16 is screwed onto the end of the barrel. The friction fit of the telescoped adapter elements is such that this operation may be accomplished by the operator grasping casing wall 19 and turning it until washer 38 is compressed to sealing condition and the stem end of the adapter device thereby effectively tightly secured to the end of barrel 11.

The torque exerted by turning casing 18 and transmitted through the frictionally engaged body 26 to stem 33 is sufficient for mounting the adapter device 16 on the barrel while adequately compressing washer 38. During this operation the differential axial forces acting on the adapter elements results in body 26 being placed in initial longitudinal tension which thereby pulls disc 27 resiliently onto seated engagement with shoulder 22 and automatic coaxial relation with the syringe barrel. Thus FIGS. 2 and 5 represent the normal arrangement of parts when the assembly is idle or initially used.

In use the hollow injection needle 17 is pushed onto tube 29 with a friction fit so that it becomes a rigid extension of tube 29, and the syringe barrel is charged. When the needle is thrust into the animal as shown in FIG. 5 the axially transmitted force is substantially direct and solid due to the firm seating of disc 27 on shoulder 22. Should the animal move so as to tend to tilt the needle relatively to the syringe axis this will result in disc 27 effectively tilting as permitted by flexure of body 26 and as illustrated in FIGS. 3 and 6. During this movement disc 27 tends to leave full seating on shoulder 22 and have some axially outward displacement relative to casing 18 as permitted by the resiliency of the body 26. In practice the disc 27 appears to rock about an edge upon an effective pivot region constituted by adjacent parts of shoulder 22 and lip 21, (see FIG. 3) and the diametrically opposite edge is displaced away from the shoulder and lip. During such rocking shoulder 22 prevents the disc from being displaced axially within the casing, while the lip prevents the disc from being laterally displaced from the casing end. Tilting of disc 27 is resiliently permitted and controlled by body 26 the wall of which undergoes increased tension at one side, and when the needle is withdrawn from the animal the tension of body 26 automatically restores the disc to the initial coaxial position of FIG. 2.

Thus in the invention the injection needle is mounted for effective tilting in response to lateral forces under control of a resilient means which also serves as a conduit for the fluid being discharged to the needle.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A device for mounting a hypodermic needle on a syringe barrel comprising a relatively stiff tubular casing having means at one end for attachment to said barrel and means at the other end for mounting a hollow needle, means defining an annular seating face at said other end of said casing, said needle mounting means comprising a rigid needle attachment member that extends transversely of said casing and has a through fluid discharge opening and an associated needle connection and is seated on said face and means in the casing normally resiliently biasing said member onto said face but permitting tilting of said member relative to said face in response to predetermined lateral forces on the needle.

2. The device defined in claim 1, wherein said resilient biasing means is a tubular body serving also as a fluid conduit extending longitudinally through said casing.

3. The device defined in claim 1, wherein said attachment means at said one end comprises a hollow threaded stem, and said resilient biasing means comprises a tubular body within said casing fixedly bonded at opposite ends to said stem and said needle attachment member to provide a fluid pressure tight conduit to said discharge opening.

4. The device defined in claim 3, wherein said body is resilient and effectively lines the internal periphery of said casing.

5. The device defined in claim 1, wherein said casing is substantially cylindrical with said other end being substantially fully open and surrounded by an axially outwardly facing shoulder forming said face, and said needle attachment member is a plate-like element extending across said open end of the casing and seated on said shoulder.

6. The device defined in claim 5, including an outwardly flared casing lip surrounding said needle attachment member.

7. A device for mounting a hypodermic needle on a syringe barrel comprising a relatively stiff tubular casing having means at one end for attachment to said barrel and means at the other end for mounting a hollow needle, said needle mounting means comprising a needle attachment member that has a through fluid discharge opening and an associated needle connection and is seated on said other end of the casing and flexible means in the casing resiliently permitting tilting of said member relative to its seat in response to predetermined lateral forces on the needle, said casing being substantially cylindrical with said other end being substantially fully open and surrounded by an axially outwardly facing shoulder, said needle attachment member being a plate-like element extending across said open end of the casing and seated on said shoulder, said means for attaching the casing to the barrel comprising a hollow stem extending through an opening in an end wall of said casing and formed with a flange within said casing, and said flexible means comprising a resilient tubular body effectively lining said casing in telescoping frictional contact therewith and bonded at opposite ends to said stem flange and said needle attachment member.

8. The device defined in claim 7, wherein said resilient body has an end wall bonded to said stem flange, and said stem is externally threaded outside said casing end wall.

9. The device defined in claim 8, wherein an axially facing ledge surrounds the opening in the casing end wall for engaging and compressing a resilient seal ring on said threaded stem portion when the device is mounted on the syringe barrel by turning said stem into a threaded outlet in the end wall of the barrel.

* * * * *